(12) United States Patent
Grant et al.

(10) Patent No.: US 7,706,912 B2
(45) Date of Patent: Apr. 27, 2010

(54) ORIFICE FORMATION CONTROL SYSTEM

(75) Inventors: Marion B. Grant, Princeville, IL (US); Nien L. Lee, Peoria, IL (US)

(73) Assignee: Caterpillar Inc., Peoria, IL (US)

( * ) Notice: Subject to any disclaimer, the term of this patent is extended or adjusted under 35 U.S.C. 154(b) by 200 days.

(21) Appl. No.: 11/987,511

(22) Filed: Nov. 30, 2007

(65) Prior Publication Data

US 2009/0143885 A1    Jun. 4, 2009

(51) Int. Cl.
- *G06F 19/00* (2006.01)
- *A61B 6/00* (2006.01)
- *G01N 23/00* (2006.01)
- *G01N 23/04* (2006.01)
- *G21K 1/12* (2006.01)
- *H05G 1/60* (2006.01)
- *G06K 9/00* (2006.01)

(52) U.S. Cl. .......... 700/159; 700/98; 700/118; 700/163; 378/4; 378/21; 378/57; 382/131; 382/149; 382/152

(58) Field of Classification Search ............. 700/97–98, 700/117–118, 120, 159, 162–163; 250/363.04, 250/363.06; 378/4, 21, 23–27, 57–58, 195; 382/131, 154, 100, 149, 152; 424/9.4; 600/425
See application file for complete search history.

(56) References Cited

U.S. PATENT DOCUMENTS

| | | | |
|---|---|---|---|
| 3,984,684 A | 10/1976 | Winnek | |
| 4,415,980 A | 11/1983 | Buchanan | |
| 4,725,963 A | 2/1988 | Taylor et al. | |
| 4,926,452 A | 5/1990 | Baker et al. | |
| 5,548,627 A * | 8/1996 | Swerdloff et al. | 378/4 |
| 5,687,208 A * | 11/1997 | Bae et al. | 378/8 |
| 5,731,820 A * | 3/1998 | Broekhuijsen | 345/442 |
| 5,825,017 A | 10/1998 | Pryor | |
| 6,252,924 B1 * | 6/2001 | Davantes et al. | 378/8 |
| 6,275,559 B1 * | 8/2001 | Ramani et al. | 378/4 |
| 6,283,997 B1 * | 9/2001 | Garg et al. | 623/16.11 |
| 6,359,956 B1 * | 3/2002 | Hsieh et al. | 378/15 |
| 6,385,286 B1 * | 5/2002 | Fitchard et al. | 378/65 |
| 6,396,613 B1 * | 5/2002 | Harrison et al. | 398/141 |
| 6,569,405 B1 * | 5/2003 | Sutton et al. | 424/9.52 |
| 6,575,969 B1 * | 6/2003 | Rittman et al. | 606/41 |
| 6,895,073 B2 | 5/2005 | Shih et al. | |
| 7,333,588 B2 * | 2/2008 | Mistretta et al. | 378/10 |
| 2008/0208161 A1 * | 8/2008 | Kaji et al. | 604/500 |
| 2008/0218588 A1 * | 9/2008 | Stetten | 348/47 |

FOREIGN PATENT DOCUMENTS

JP    2000-310682 A    11/2000

\* cited by examiner

*Primary Examiner*—Ramesh B Patel
(74) *Attorney, Agent, or Firm*—Finnegan, Henderson, Farabow, Garrett & Dunner

(57) ABSTRACT

An orifice formation system is provided. The system includes a manufacturing machine configured to form an orifice in a workpiece, a computed tomography x-ray machine configured to generate data based on geometry of the workpiece, and a computer in communication with the manufacturing machine and the computed tomography x-ray machine. The computer is configured to control the manufacturing machine based on the data generated by the computed tomography x-ray machine. A method of controlling formation of an orifice in a workpiece is also provided. The method includes acquiring computed tomography data about the workpiece, determining geometry of the workpiece based on the computed tomography data, and forming an orifice in the workpiece based on the determined geometry of the workpiece.

21 Claims, 4 Drawing Sheets

ORIFICE FORMATION CONTROL SYSTEM

TECHNICAL FIELD

The present disclosure relates to a control system and, more particularly, to an orifice formation control system.

BACKGROUND

Machine components are often manufactured based on the physical and/or functional characteristics that define their desired operation. High quality, precise manufacturing is used to ensure that components will operate as expected and within acceptable tolerances. To verify that components are manufactured according to their specified criteria, manufacturers often perform quality control inspections during and/or following a manufacturing process.

For example, fuel injectors must be manufactured with predetermined dimensions in order to be compatible with a host machine. Further, fuel injectors must be manufactured so that they inject precise amounts of fuel in a manner required for efficient operation of the machine. Therefore, fuel injectors having high-tolerance, small-diameter fuel injector orifices are often manufactured in large quantities. In the manufacture of these fuel injectors, various metrology devices and methods have been used to confirm the geometry of orifices formed in the nozzles of the fuel injectors. Some of these devices include, for example, gage wires, optical measuring microscopes, coordinate measuring machines (CMMs), and Werth machines. Functional measurement has also been used, such as by spraying fuel through the nozzle orifices in a test environment to determine the accuracy and precision of the drilled orifices. Although many of these devices and methods may provide somewhat accurate results, they require human intensive operations, involve little or no automation, and cannot provide consistently repeatable precision.

Recently, attempts have been made to automate the quality-control inspection of various manufactured components by using computed tomography (CT) x-ray imaging. For example, U.S. Pat. No. 6,895,073 (the '073 patent), issued to Shih et al. on May 17, 2005, discloses a high-speed x-ray inspection apparatus and method. The system of the '073 patent includes three CT x-ray sources and an x-ray detector configured to obtain two-dimensional images of a manufactured component. The images are compared to one or more calibration images of the component, whereby components exceeding a certain threshold are designated as "defective." Because the system only obtains a limited number of 2-D images, processing time is reduced and automated quality control of the component is expedited.

Although the '073 patent discloses the automated CT x-ray quality control of manufactured components, its usefulness may be limited. Specifically, the number of images provided by the system of the '073 patent may be insufficient to generate a high-resolution image that accurately represents the component. Further, the obtained 2-D images are only compared to the calibration images to determine if a threshold level of accuracy is obtained, without any feedback being provided to the manufacturing process. Therefore, the system may be unable to improve the quality of the manufacturing process itself and the resulting tolerances of the manufactured components.

The present disclosure is directed to overcoming one or more of the shortcomings set forth above.

SUMMARY

In one aspect, the present disclosure is directed to an orifice formation control system. The system includes a manufacturing machine configured to form an orifice in a workpiece, a computed tomography x-ray machine configured to generate data based on geometry of the workpiece, and a computer in communication with the manufacturing machine and the computed tomography x-ray machine. The computer is configured to control the manufacturing machine based on the data generated by the computed tomography x-ray machine.

In another aspect, the present disclosure is directed to a method of controlling formation of orifices in a workpiece. The method includes forming an orifice in the workpiece and generating a plurality of cross-sectional workpiece images, with each image intersecting a central axis of the workpiece and corresponding to one of a plurality of discrete angular steps. The method further includes determining geometry of the orifice based on the plurality of cross-sectional workpiece images, and forming at least one additional orifice in the workpiece based on determined geometry of the orifice.

In yet another aspect, the present disclosure is directed to a method of controlling formation of an orifice in a workpiece. The method includes acquiring computed tomography data about the workpiece, determining geometry of the workpiece based on the computed tomography data, and forming an orifice in the workpiece based on the determined geometry of the workpiece.

DETAILED DESCRIPTION

Figure 1:
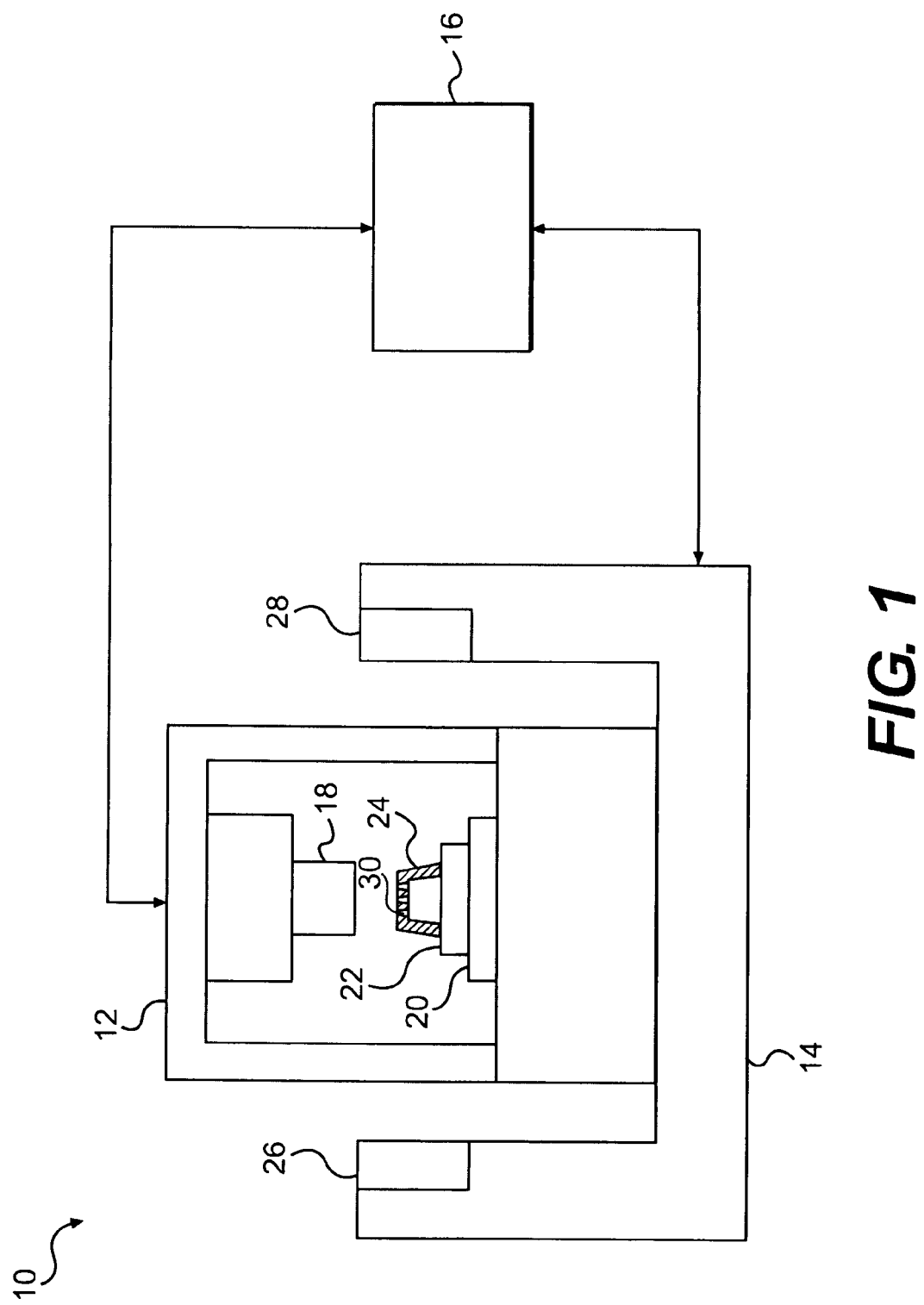
FIG. 1 is a diagrammatic illustration of an exemplary disclosed orifice formation control system.

FIG. 1 illustrates an orifice formation control system 10. Orifice formation control system 10 may include a drilling machine 12, a computed tomography (CT) x-ray machine 14, and a computer 16. In general, CT x-ray machine 14 may be configured to obtain data from a workpiece 24 disposed on drilling machine 12, while computer 16 may be configured to analyze the data and provide corresponding feedback signals to drilling machine 12.

Drilling machine 12 may be any type of known drilling machine capable of forming one or more orifices 30 in a workpiece 24. For example, drilling machine 12 may be a laser drilling device, which may form deep, small-diameter holes by irradiating workpiece 24 with many short pulses of laser light. In one embodiment, drilling machine 12 may be an ExOne Superpulse® laser drilling device. Drilling machine 12 may alternatively be an electrical discharge machining (EDM) machine, such as a wire, "die-sinking", plunge, or vertical-type EDM machine. As depicted in FIG. 1, drilling machine 12 may include an end effector 18, which may be any type of drilling tool, such as a laser (in the case of a laser drilling device) or an electrode (in the case of an EDM machine). Yet further alternatives of drilling machine 12 may include a water jet machine, a conventional-type drill, or any other drilling machine having an end effector 18 capable of forming orifice 30 in workpiece 24.

Drilling machine 12 may also include a turntable 20 and a collet 22 configured to retain workpiece 24 in alignment with end effector 18. Turntable 20 may include any rotatable mechanism, such as an air bearing or ball bearing, configured to rotate collet 22 and a workpiece 24, which may be retained therein. Collet 22 may be any type of vise or other suitable clamp, so long as it retains workpiece 24 sufficiently immobile to obtain desirable machine tolerances. It is further desirable that workpiece 24 be retained in a manner that sufficiently reduces vibration and other disturbances. Workpiece 24 may also be in communication with a power supply, dielectric fluid, or any other conductor or insulator, as desired, given a particular type of drilling machine 12 employed. In one embodiment, workpiece 24 may be an injector nozzle of a fuel injector for a diesel fuel engine. Alternatively, workpiece 24 may be a turbine blade or any other component benefiting from one or more reverse tapered orifices.

CT x-ray machine 14 may by any type of machine suitable for performing high-resolution, three-dimensional imaging of workpiece 24. As illustrated in FIG. 1, CT x-ray machine 14 may include a radiation emitter 26 and a radiation detector 28. In one embodiment, radiation emitter 26 and radiation detector 28 may be fixed relative to workpiece 24. In another embodiment, radiation emitter 26 and radiation detector 28 may be configured to rotate, for example, about 360 degrees around workpiece 24 (i.e., around a vertical or horizontal axis passing through workpiece 24). Radiation emitter 26 may include any suitable type of x-ray tube, such as for example, a 100-500 kV, high-power or micro-focus x-ray tube. Moreover, radiation emitter 26 may include a plurality of radiation tubes, or sources. Radiation detector 28 may be a digital detector configured to detect radiation emitted from radiation emitter 26, as affected by the geometry of workpiece 24. For example, radiation detector 28 may include a 1-10 Megapixel digital radiation detecting mechanism. In one embodiment, radiation detector 28 may include an array, or plurality, of digital detectors configured to cooperate with corresponding radiation emitters 26. CT x-ray machine 14 may include a built-in processor configured to control the operation of radiation emitter 26 and/or radiation detector 28. CT x-ray machine may also include built-in processing for data storage, component feature extraction, volume reconstruction, rendering/visualization, dimensional analysis, and/or model comparison. In one embodiment, CT x-ray machine 14 may further include a built-in display monitor for displaying three-dimensional representations of inspected components.

Although drilling machine 12 and CT x-ray machine 14 are depicted in FIG. 1 as being adjacent and cooperatively disposed about workpiece 24, they may also be completely separate and remotely disposed. For example, CT x-ray machine 14 may be a stationary x-ray system which is installed in a fixed location, or a mobile, or translatable, x-ray system. In this embodiment, workpiece 24 may be partially or fully manufactured by drilling machine 12 and then transferred to CT x-ray machine 14 for inspection. In an alternative embodiment, drilling machine 12, CT x-ray machine 14, and computer 16 may be packaged as a fully integrated drilling and inspection system.

Computer 16 may be disposed in communication with drilling machine 12 and CT x-ray machine 14. Computer 16 may include a single microprocessor or multiple microprocessors that include means for controlling the operation of drilling machine 12 and/or CT x-ray machine 14. Numerous commercially available microprocessors may perform the functions of computer 16. It should be appreciated that computer 16 could readily embody a general machine microprocessor capable of controlling numerous machine functions. Computer 16 may include or be associated with a memory for storing data such as for example, an operating condition, a design limit, and a performance characteristic or specification of drilling machine 12, CT x-ray machine 14, and/or workpiece 24. Various other known circuits may be associated with computer 16, including power supply circuitry, signal-conditioning circuitry, solenoid driver circuitry, communication circuitry, and other appropriate circuitry. Moreover, because computer 16 may communicate with other components via either wired or wireless transmission, computer 16 may be disposed in a location remote from drilling machine 12, if desired. Alternatively, as discussed above, computer 16 may be integral with CT x-ray machine 14. Accordingly, computer 16 may be configured to receive signals from CT x-ray machine 14 including CT data about the geometry of workpiece 24. Computer 16 may be configured to analyze the CT data and send feedback signals to drilling machine 14 based on the analyzed CT data.

Figure 2:
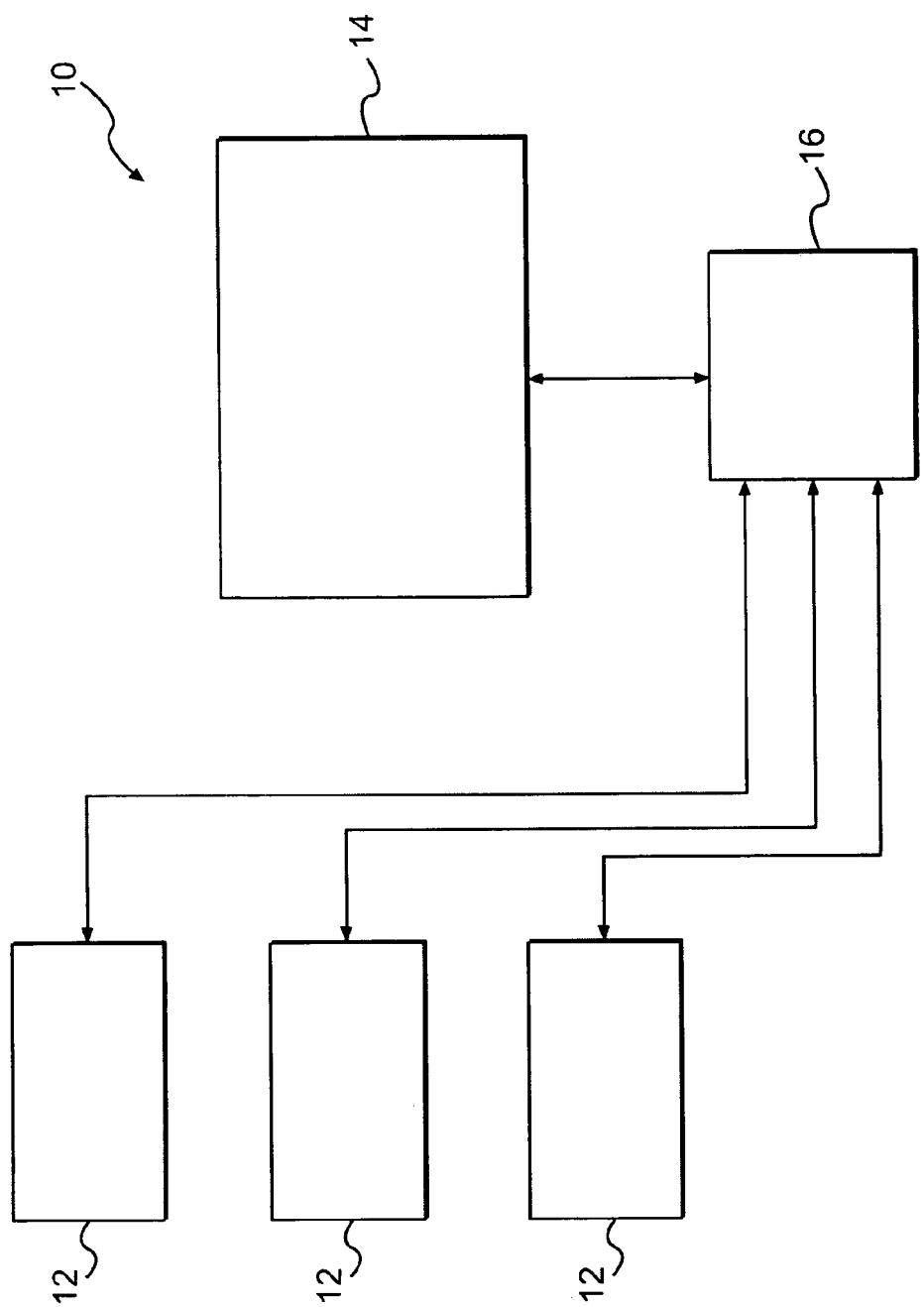
FIG. 2 is a diagrammatic illustration of another exemplary disclosed orifice formation control system.

FIG. 2 illustrates an embodiment of the present disclosure in which a single CT x-ray machine 14 is configured to operate with a plurality of drilling machines 12. Specifically, CT x-ray machine 14 may selectively bring each drilling machine 12 into its line-of-sight (i.e., between a radiation emitter/detector pair of the x-ray machine). Alternatively, CT x-ray machine 14 may be stationary, whereby workpieces of the various drilling machines 12 are moved into the line-of-sight of CT x-ray machine 14, either with a respective drilling machine 12 or not. As illustrated in FIG. 2, computer 16 may be in communication with CT x-ray machine 14 and the plurality of drilling machines 12. Accordingly, CT x-ray machine 14 may be configured to generate geometric information about workpieces 24 associated with the plurality of drilling machines 12. Computer 16 may be configured to receive the geometric workpiece information generated by CT x-ray machine 14. Computer 16 may be further configured to direct signals to the plurality of drilling machines 12 based on the geometric workpiece information.

Figure 3:
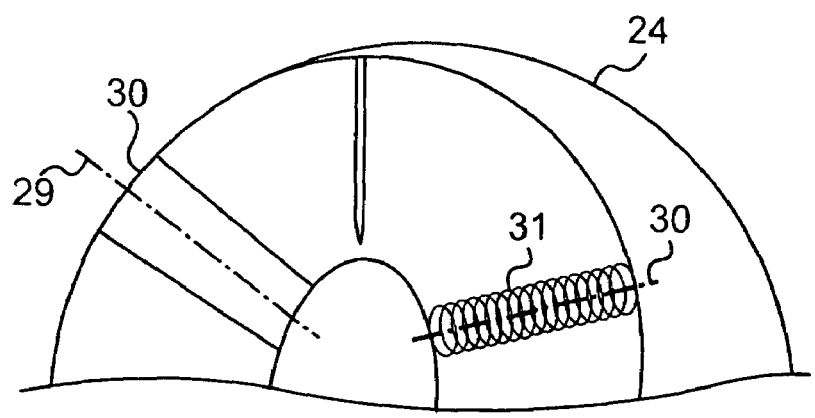
FIGS. 3 and 4 are diagrammatic representations of exemplary disclosed workpieces having orifices formed by one of the control systems of FIGS. 1 and 2.
Figure 4:
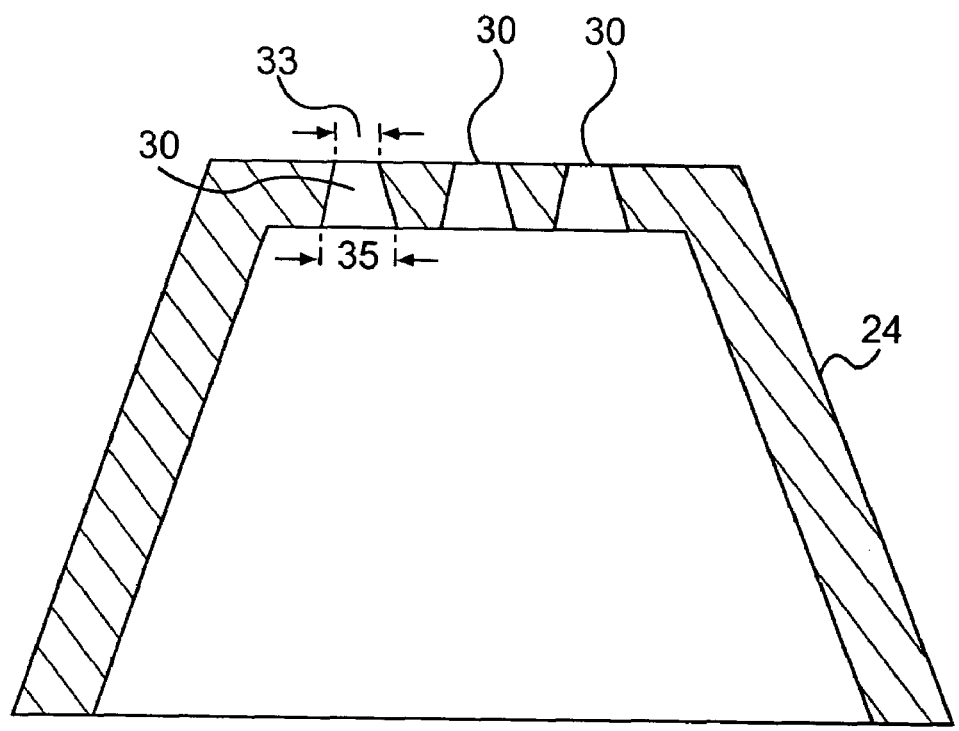

As described above with respect to FIG. 1, drilling machine 12 may be configured to form one or more orifices 30 into workpiece 24. FIGS. 3 and 4 illustrate cross-sections of exemplary workpieces 24 having a plurality of orifices 30 formed therein. Computer 16 may be configured to analyze dimensions of each orifice 30. For example, as illustrated in FIG. 3, software of computer 16 may be used to cut a half-section of orifice 30 and perform a "least-squares" line analysis to determine the straightness of a center-line 29 of orifice 30. Alternatively, the dimensional analysis software may take around 20 to 30 "slices" along a length of each orifice 30, and perform a "least squares" circle analysis 31 to determine a roundness of the orifice. In one embodiment, workpiece 24 may be a fuel injector nozzle having orifices 30, each orifice 30 having a reverse taper profile and a diameter in the range of 100 to 500 μm. As exaggerated in the embodiment of FIG. 4, orifices 30 may have an inner diameter 35, which may be larger than an outer diameter 33. For example, in an orifice having a diameter on the order of 200 μm, the dimensional difference between the inner diameter 35 and outer diameter 33 may be approximately 10 to 70 μm. Accordingly, orifices 30 with such precisely controlled dimensions may be able to generate a desirable spray of a liquid, such as a fuel, through workpiece 24.

Figure 5:
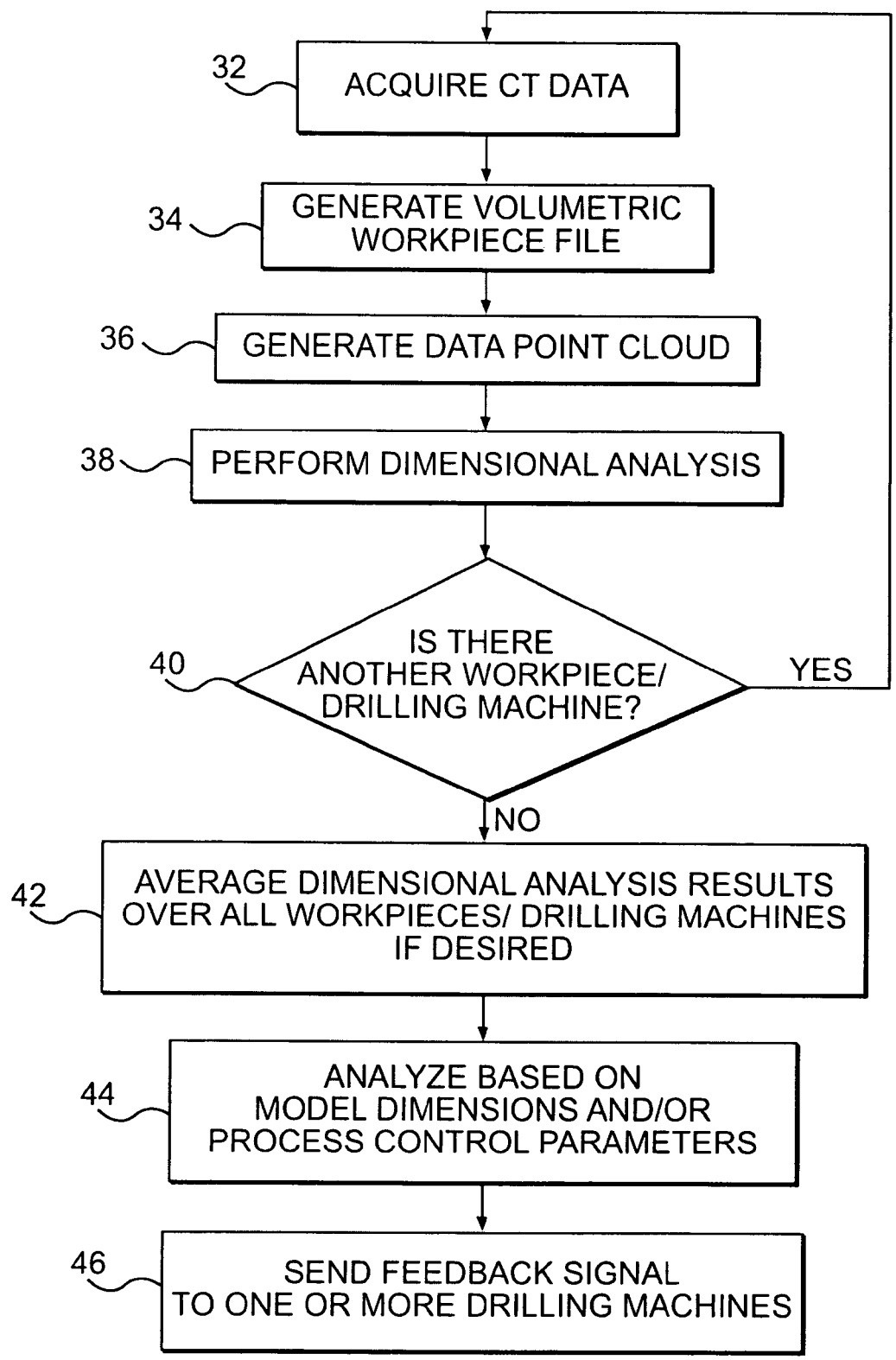
FIG. 5 is a flowchart illustrating an exemplary disclosed method for forming orifices in a workpiece.

FIG. 5 depicts steps of an exemplary method of forming orifices 30 within workpiece 24, using system 10 of FIG. 1 or 2. FIG. 5 will be described in detail in the following section to better illustrate the disclosed system and its operation.

INDUSTRIAL APPLICABILITY

The disclosed system may be used to produce orifices, such as reverse tapered orifices, in an automated, efficient, and precise manner. Because the system uses computed tomography x-ray inspection of workpieces, the system may perform high-resolution metrology of one or more orifices within one or more workpieces. Moreover, because the system is in communication with the orifice formation process, it may provide feedback to the orifice formation process based on the high-resolution metrology. Therefore, the accurate formation of an orifice within a workpiece may be improved based upon metrology of another workpiece, metrology of another orifice within the same workpiece, or even metrology of the very same orifice. Accordingly, the formation of high-tolerance orifices may be performed without a substantial amount of human intervention and without a need for repeated measurements. The operation of orifice formation control system 10 will now be described.

Referring now to FIGS. 1 and 4, during or after a process by which drilling machine 12 forms one or more orifices 30 in workpiece 24, CT x-ray machine 14 may acquire computed tomography data about the geometry of workpiece 24 (step 32). To acquire this data, turntable 20 may intermittently rotate workpiece 24 by 360 degrees, in half-degree increments about a central axis of workpiece 24. CT x-ray machine 14 may use radiation emitter 26 and radiation detector 28 to generate a cross-sectional workpiece image corresponding to each of the half-degree increments. Accordingly, CT x-ray machine 14 may generate 720 images, or "slices," of workpiece 24, each image being a two-dimensional representation of the features of workpiece 24 across a particular, rotationally-oriented plane.

Either CT x-ray machine 14 or computer 16 may then generate a volumetric workpiece file representing the physical characteristics of workpiece 24 (step 34). Specifically, CT x-ray machine 14 may communicate the acquired CT data to computer 16, to be assembled into a three-dimensional, volumetric workpiece file. Alternatively, the volumetric workpiece file may be generated by a processor built-in to CT x-ray machine 14.

Either CT x-ray machine 14 or computer 16 may then generate a data point cloud from the volumetric workpiece file (step 36). Specifically, the volumetric workpiece file may be converted into a data point cloud by various statistical and geometrical methods, with each data point in the cloud representing an approximate location of a point on workpiece 24. For example, each orifice 30 may be represented by approximately 10,000 data points defining a cylindrical shell of the orifice. Even in the event that a selected type of CT x-ray machine 14 only obtains each data point to 6 or 7 µm, the analysis of thousands of neighboring data points may be used to improve the imaging resolution to the micron level. For example, statistical averages and probabilities may be used to optimize an approximated location for a data point. Accordingly, the geometry of each orifice 30, and even workpiece 24, may be determined to a resolution as low as 0.5-2.0 µm.

Either CT x-ray machine 14 or computer 16 may then perform dimensional analysis on the data point cloud (step 38). For example, software may be used to cut multiple cross-sections of orifice 30 and perform "least-squares" circular fits at each level to determine: diameter vs. position along the hole length; roundness of the hole as a function of hole depth; and/or straightness of a center-line 29 formed by the centers of the circles of orifice 30. Alternatively, the dimensional analysis software may take up to around 30 planar "slices" along a length of each orifice 30, with each planar "slice" containing the center-line of the hole. A "least squares" straight line may be fit to the planar slices to determine: side wall angles of orifice 30; relative angles between opposite sides of orifice 30; and/or side wall straightness of orifice 30. Such dimensional analysis may therefore reveal the size, location, orientation, axial profile, chamfer geometry and/or reverse taper geometry, for each orifice 30.

The above-described steps of: generating the volumetric workpiece file, generating the data point cloud, and performing dimensional analysis may be performed within CT x-ray machine 14 or by computer 16. Alternatively, each step may be performed on a separate computer 16, separate processor, and/or a separate software package, in a so-called "parallel processing" or "pipe-lining" process. Because the processing steps may be divided across distinct computers, processors, and/or software suites, the processing of data in these steps may be expedited to a pace that may make possible the real-time imaging of workpiece 24 and any orifices 30. In one exemplary embodiment, processing may be done at a rate of one fuel injector per thirty minutes, such that statistical analysis and feedback may be possible.

In another exemplary embodiment, processing may be performed at a rate sufficient to provide feedback for drilling machine 12 to adjust the formation of the very same orifice 30 being imaged and analyzed. For example, CT x-ray machine 14 may be configured to generate geometric information about orifice 30 while it is being formed. CT x-ray machine 14 may analyze the geometric information to determine whether the formation process of orifice 30 should be modified, such as by modifying the orientation, pathway, speed, or material removal rate of end effector 18 of drilling machine 12. CT x-ray machine 14 may also be configured to re-form portions of orifice 30 that do not fall within certain pre-defined dimensional tolerances relative to an ideal model of orifice 30.

Having obtained a dimensional analysis of workpiece 24, computer 16 may then determine whether there is another workpiece 24 or drilling machine 12 for which dimensional analysis is desired (step 40). For example, in the event that computer 16 is in communication with a plurality of drilling machines 12, as illustrated in FIG. 2, CT x-ray machine 14 and/or computer 16 may continue to perform the looped steps of acquiring CT data (step 32), generating a volumetric workpiece file (step 34), generating a data point cloud (step 36), and performing a dimensional analysis (step 38) for workpieces 24 associated with each drilling machine 12, until all desired workpieces 24 have been imaged and analyzed.

Computer 16 may then average the dimensional analysis results across all desired workpieces 24 to obtain a statistical solution for the geometric formation of orifices 30 in workpieces 24 (step 42). For example, computer 16 may average the dimensional analysis results across several workpieces 24 manufactured from a single drilling machine 12. Alternatively, computer 16 may average the dimensional analysis results across several workpieces 24. In one embodiment, the dimensional analysis results may be averaged across all of the orifices 30 in a single workpiece 24.

Computer 16 may analyze the averaged dimensional analysis results based on an ideal model for orifice geometry and/or known process control parameters of drilling machine 12 (step 44). For example, computer 16 may compare the averaged dimensional analysis results to an ideal model, or the theoretical orifice dimensions that were designed and intended for drilling machine 12 to produce. In one embodiment, computer 16 may determine the specific differences between the averaged dimensional analysis results and the model orifice dimensions. Computer 16 may then calculate the process control changes necessary to compensate for those differences, in view of certain known parameters about the particular drilling process. For example, computer 16 may take into account the dwell time, material removal rate, tool wear rate, material properties, tool orientation, tool rate, and other physical properties and parameters which affect resulting orifice dimensions, given a certain process implemented by drilling machine 12.

Accordingly, computer 16 may then send feedback information to one or more drilling machines 12 (step 46). Specifically, computer 16 may send signals to one or more drilling machines 12, which contain sufficient information to advantageously update the manufacturing process. For example, computer 16 may send updated information about the condition of the tool or workpieces 24. Alternatively, computer 16 may send information that adjusts the physical path or speed of the end effector 18 of the particular drilling machine 12. Accordingly, the operation of drilling machine 12 may be updated with real-time and/or statistical feedback about the high-resolution metrology of various workpiece orifices. This may allow drilling machines 12 to be "re-targeted" or calibrated in a more efficient and effective manner, resulting in more accurate and precise injector orifices.

The presently disclosed orifice formation control system may reliably and advantageously create reverse tapered injector nozzle orifices in a more automated, efficient and repeatable manner. Because computed tomography x-ray imaging is used for determining workpiece geometry, relatively little manual labor needs to be used in measuring workpiece feature dimensions. Moreover, because CT x-ray measurement is accurate and precise, duplicative measurements may be avoided. Finally, the system provides statistical and/or real-time feedback control of orifice formation, which increases the rate at which high tolerance orifices may be manufactured. Accordingly, the disclosed system provides appreciable improvements in the cost and time-commitment associated with performing such high quality manufacturing processes.

It will be apparent to those skilled in the art that various modifications and variations can be made to the disclosed orifice formation control system. Other embodiments will be apparent to those skilled in the art from consideration of the specification and practice of the disclosed orifice formation control system. It is intended that the specification and examples be considered as exemplary only, with a true scope being indicated by the following claims and their equivalents.

What is claimed is:

1. An orifice formation system, comprising:
   a manufacturing machine configured to form an orifice in a workpiece;
   a computed tomography x-ray machine configured to generate data based on geometry of the workpiece; and
   a computer in communication with the manufacturing machine and the computed tomography x-ray machine, the computer being configured to control the manufacturing machine based on the data generated by the computed tomography x-ray machine.

2. The system of claim 1, wherein the manufacturing machine is an EDM machine.

3. The system of claim 1, wherein the manufacturing machine is a laser drilling device.

4. The system of claim 1, further including a turntable configured to rotate the workpiece relative to the computed tomography x-ray machine.

5. The system of claim 1, further including at least one additional manufacturing machine, each at least one additional manufacturing machine being configured to form an orifice in a workpiece, wherein the computed tomography x-ray machine is configured to generate computed tomography data for the workpieces with the manufacturing machine and the at least one additional manufacturing machine.

6. The system of claim 5, wherein the computer is configured to receive the computed tomography data generated by the computed tomography x-ray machine and analyze dimensions of the workpiece based on the data.

7. The system of claim 6, wherein the computer is configured to modify operation of the manufacturing machine and the at least one additional manufacturing machine in response to analyzed dimensions of the workpiece.

8. A method of controlling formation of orifices in a workpiece, comprising:
   forming an orifice in a workpiece;
   generating a plurality of cross-sectional workpiece images, each image intersecting a central axis of the workpiece and corresponding to one of a plurality of discrete angular steps;
   determining geometry of the orifice based on the plurality of cross-sectional workpiece images; and
   forming at least one additional orifice in the workpiece based on the determined geometry of the orifice.

9. The method of claim 8, wherein determining geometry of the orifice includes calculating a least-squares line at a center of the orifice.

10. The method of claim 8, wherein determining geometry of the orifice includes calculating least-squares circles at various depths of the orifice.

11. The method of claim 8, further including comparing determined geometry of the orifice to ideal orifice geometry.

12. A method of controlling formation of an orifice in a workpiece, the method comprising:
    acquiring computed tomography data about the workpiece;
    determining geometry of the workpiece based on the computed tomography data; and
    forming an orifice in the workpiece based on the determined geometry of the workpiece.

13. The method of claim 12, wherein acquiring computed tomography data includes intermittently rotating the workpiece about a central axis in a plurality of discrete angular steps, and generating a cross-sectional workpiece image corresponding to each angular step.

14. The method of claim 12, wherein determining geometry of the workpiece comprises:
    generating a volumetric workpiece file based on the acquired computed tomography data;
    generating a data point cloud based on the volumetric workpiece file; and
    analyzing dimensions of the data point cloud.

15. The method of claim 12, wherein forming an orifice in the workpiece based on the determined geometry includes modifying one or more of a dwell time, material removal rate, tool orientation, and tool rate.

16. The method of claim 12, wherein the method further comprises:
    acquiring computed tomography data about a second workpiece;
    determining geometry of the second workpiece based on the computed tomography data;
    determining averaged workpiece geometry based on geometry of the first and second workpieces; and
    affecting orifice formation of a third workpiece based on the averaged workpiece geometry.

17. The method of claim 14, wherein analyzing dimensions of the data point cloud includes calculating a least-squares line at a center of the orifice.

18. The method of claim 14, wherein analyzing dimensions of the data point cloud includes calculating least-squares circles at various depths of the orifice.

19. The method of claim 14, wherein analyzing dimensions of the data point cloud includes comparing the dimensions of the data point cloud to ideal workpiece dimensions.

20. The method of claim 14, wherein analyzing dimensions of the data point cloud further includes consideration of a physical property of one or more of the workpiece and a machine tool.

21. A method of controlling formation of an orifice in a workpiece, the method comprising:
   acquiring computed tomography data about the workpiece;
   determining geometry of the workpiece based on the computed tomography data; and
   modifying manufacturing of one of the workpiece and a subsequent workpiece based on the determined geometry of the workpiece.

* * * * *